United States Patent
Iwao et al.

(10) Patent No.: US 9,326,952 B2
(45) Date of Patent: May 3, 2016

(54) ADHESIVE SKIN PATCH

(75) Inventors: Yoshihiro Iwao, Osaka (JP); Kensuke Matsuoka, Osaka (JP); Kazuhiro Aoyagi, Osaka (JP)

(73) Assignee: NITTO DENKO CORPORATION, Osaka (JP)

( * ) Notice: Subject to any disclaimer, the term of this patent is extended or adjusted under 35 U.S.C. 154(b) by 0 days.

(21) Appl. No.: 13/581,079

(22) PCT Filed: Feb. 23, 2011

(86) PCT No.: PCT/JP2011/054043
§ 371 (c)(1),
(2), (4) Date: Aug. 24, 2012

(87) PCT Pub. No.: WO2011/105457
PCT Pub. Date: Sep. 1, 2011

(65) Prior Publication Data
US 2012/0323191 A1  Dec. 20, 2012

(30) Foreign Application Priority Data
Feb. 26, 2010 (JP) ................................. 2010-043100

(51) Int. Cl.
*A61F 13/00* (2006.01)
*A61K 9/70* (2006.01)

(52) U.S. Cl.
CPC ............... *A61K 9/7061* (2013.01); *A61K 9/703* (2013.01); *A61K 9/7053* (2013.01); *A61F 2013/00651* (2013.01); *A61K 9/7023* (2013.01)

(58) Field of Classification Search
CPC .............. A61F 13/02; A61F 13/0203; A61F 2013/00651; A61K 9/703; A61K 9/7023; A61K 9/7038; A61K 9/7084; A61K 9/7092; A61K 9/7076; A61K 9/7053; A61L 15/58
USPC .......... 604/289, 301, 304–308; 424/448, 449; 206/440, 441, 477, 813
See application file for complete search history.

(56) References Cited

U.S. PATENT DOCUMENTS 3,699,963 A * 10/1972 Zaffaroni ...................... 424/435
4,281,650 A * 8/1981 Spiegelberg .................. 206/440
(Continued)

FOREIGN PATENT DOCUMENTS

CN   101219088 A   7/2008
EP   2 198 817 A1   6/2010
(Continued)

OTHER PUBLICATIONS

Office Action, dated Apr. 1, 2013, issued by the State Intellectual Property Office of the People's Republic of China in counterpart Chinese Application No. 201180011070.1.
(Continued)

*Primary Examiner* — Tatyana Zalukaeva
*Assistant Examiner* — Ariana Zimbouski
(74) *Attorney, Agent, or Firm* — Sughrue Mion, PLLC

(57) ABSTRACT

The invention is intended to provide an adhesive patch which contains a drug except bisoprolol and which effectively inhibits the occurrence of oozing out or sticking out of the adhesive layer components from the exposed area of the adhesive layer of the adhesive patch during storage as well as the occurrence of oozing out of the drug from the adhesive layer thereby preventing the reduction in drug content. The support, the release liner and the adhesive layer constituting the adhesive patch each are formed to have a rectangular planar shape and the entire adhesive patch are formed to have a rectangular planar shape, and a protrudent part is formed on the support-side surface of the adhesive patch at a corner thereof. In addition, the adhesive patch may be formed to have a middle part and a peripheral part, and the protrudent part may be formed at a corner of the rectangular middle part. Further, between the adjacent at least two protrudent parts, a connecting built-up part may be provided in which the thickness of the adhesive patch is smaller than the thickness of the adhesive patch in the protrudent part. In case where the release liner has a split part, the split part is made so as not to traverse the protrudent part.

7 Claims, 3 Drawing Sheets

(56) References Cited

U.S. PATENT DOCUMENTS

| | | | |
|---|---|---|---|
| 4,908,213 A * | 3/1990 | Govil et al. | 424/447 |
| 5,115,913 A * | 5/1992 | Anhauser et al. | 206/447 |
| 5,591,447 A | 1/1997 | Jensen | |
| 5,704,905 A * | 1/1998 | Jensen et al. | 602/58 |
| 6,093,419 A | 7/2000 | Rolf | |
| 8,247,635 B2 * | 8/2012 | Sigurjonsson et al. | 602/54 |
| 8,252,971 B2 * | 8/2012 | Aali et al. | 602/56 |
| 2005/0215934 A1 | 9/2005 | Bracht | |
| 2006/0234581 A1 * | 10/2006 | Saito et al. | 442/149 |
| 2007/0158227 A1 | 7/2007 | Amano et al. | |
| 2008/0172015 A1 | 7/2008 | Okada et al. | |
| 2009/0169603 A1 | 7/2009 | Iwao et al. | |
| 2010/0056972 A1 * | 3/2010 | Harima et al. | 602/52 |
| 2010/0158991 A1 | 6/2010 | Okada et al. | |
| 2011/0027353 A1 * | 2/2011 | Cronk et al. | 424/451 |
| 2011/0104215 A1 * | 5/2011 | Ito et al. | 424/400 |

FOREIGN PATENT DOCUMENTS

| | | |
|---|---|---|
| JP | 59-48612 U | 3/1984 |
| JP | 1-155428 U | 10/1989 |
| JP | 3-43372 A | 2/1991 |
| JP | 5-503871 A | 6/1993 |
| JP | 6-63071 A | 3/1994 |
| JP | 2000-037413 A | 2/2000 |
| JP | 2005-185559 A | 7/2005 |
| JP | 2008-188414 A | 8/2008 |
| JP | 2010-53064 A | 3/2010 |
| WO | 2005/072716 A1 | 8/2005 |
| WO | 2007/069662 A1 | 6/2007 |
| WO | 2009026135 A2 | 2/2009 |
| WO | WO2009119673 * | 10/2009 |

OTHER PUBLICATIONS

International Search Report for PCT/JP2011/054043 dated Apr. 5, 2011 [PCT/ISA/210].

Written Opinion for PCT/JP2011/054043 dated Apr. 5, 2011 [PCT/ISA/237].

Office Action dated Dec. 10, 2013, issued by the State Intellectual Property Office of the People's Republic of China in counterpart Chinese Application No. 201180011070.1.

Communication from the Russian Patent Office dated Feb. 5, 2014, in a counterpart Russian application No. 2012141031/15.

Communication dated Aug. 21, 2014, issued by the Australian Patent Office in counterpart Australian Application No. 2011221292.

Supplementary European Search Report dated Mar. 26, 2015 in European Application No. 11747417.1.

Communication dated Dec. 18, 2015, issued by the Canadian Intellectual Property Office in counterpart Canadian Application No. 2,791,196.

* cited by examiner (a)

(b)

(a)

(b)

ADHESIVE SKIN PATCH

TECHNICAL FIELD

The present invention relates to a transdermal adhesive patch suitable for continuous administration of drug except bisoprolol into a body via the skin surface.

BACKGROUND ART

Recently, a transdermal therapeutic system (TTS) for treatment or prevention of disease through transdermal absorption of drug has become recognized as one drug delivery system (DDS). In TTS, not only drug for local action but also drug administration expected for systemic action has been tried, and some have already been a commercial reality.

Transdermal preparations can evade, for example, first-pass drug metabolism in liver and various adverse reactions and, in addition, enable long-term and sustainable drug administration. Among them, an adhesive patch that contains a drug in an adhesive has been considerably developed as facilitating drug administration and enabling strict dose control.

An adhesive patch generally includes a support formed of a woven fabric, a nonwoven fabric, a plastic film or the like and, as laminated on the support, a drug-containing adhesive layer, and generally in a form of having a release liner laminated on the adhesive layer, it is kept in a package formed of a package material of a resin film or the like, and provided to user.

As one characteristic feature thereof, a recent tendency toward adhesive patches is that a soft and velvety adhesive layer, for example, an adhesive layer containing a large quantity of a liquid component held therein is employed therein for the purpose of enhancing the soft touch of the patch in sticking to skin, or for the purpose of reducing skin irritation to be caused by horny layer removal in peeling the patch, or for the purpose of increasing the solubility and the skin permeability of the drug in the adhesive layer. In such adhesive patches, "cold flow", or that is, oozing out or sticking out of the adhesive layer component from the exposed area of the adhesive layer of the adhesive patch becomes a problem.

Cold flow occurs depending on the characteristics of the adhesive layer, and often occurs during long-term storage in a state where a load is given to adhesive patches for a long period of time, or that is, in a state where an adhesive patch is packed in a package.

When cold flow occurs in an adhesive patch, the drug may flow out along with the adhesive layer component from the exposed area of the adhesive layer of the adhesive patch and, as a result, the amount of the drug contained in the adhesive patch may reduce, therefore unfavorably resulting in drug efficacy reduction. In addition, the adhesive layer component having oozed out or stuck out may adhere to the inner face of the package, therefore causing negative influences on the adhesive patch in that the adhesive patch could be poorly taken out of the package and that the adhesive patch may peel off or may get dirty during wear to skin. Further, in case where the adhesive layer is thick, the tendency is remarkable since the amount of the adhesive layer component is large. Accordingly, in adhesive patches, it is desirable that cold flow hardly occurs and the adhesive layer can sustain its original shape.

Against the above-mentioned problems, Patent Reference 1 discloses a technique for a skin adhesive material, in which the thickness of the skin adhesive layer positioned at the middle part of the support film is controlled to fall within a range of from 0.2 mm to 0.5 mm and the peripheral part thereof is pressed to reduce the thickness of the skin adhesive layer to 0.05 mm to 0.2 mm, thereby preventing the skin adhesive layer from sticking out from the edges of the skin adhesive material and preventing the edges of the skin adhesive material from peeling away.

More precisely, the method for producing the skin adhesive material described in Patent Reference 1 is characterized in that a skin adhesive layer is formed on a release sheet and a support film is laminated thereon, and the resulting laminate sheet is blanked in two stages, wherein after the first-stage blanking, the pressing to form the thin peripheral part is carried out without heating. Namely, in case where the laminate sheet is first pressed and thereafter blanked into the final shape in one stage, the skin adhesive layer positioned between the support film and the release sheet could hardly move to both sides in pressing, and even if the layer could move, it could not have an escape route, and therefore the part of the skin adhesive layer adjacent to the peripheral part may rise by pressing. Therefore, for evading the formation of the rise, the method described in Patent Reference 1 is characterized in that the previous blanking into a larger size is followed by the pressing so as to extrude the skin adhesive layer adjacent to the peripheral part from the blanked edges and the second-stage blanking gives the final shape.

However, regarding the skin adhesive material described in Patent Reference 1, during storage thereof in a package, the opportunity for the exposed part of the adhesive layer such as the edges of the skin adhesive material to be in contact with the inner surface of the package could not be reduced sufficiently, and therefore, in case where the skin adhesive layer has oozed out or stuck out from the exposed part of the adhesive layer of the skin adhesive material in the package, the adhesion of the skin adhesive material to the inner surface of the package could not be sufficiently prevented and, as a result, the skin adhesive material could hardly be taken out of the package. In addition, when the skin adhesive material could be brought into contact with clothes and others while kept stuck to skin, the opportunity for the edges of the skin adhesive material to be rubbed against the clothes and others could not be fully reduced, and the edges of the skin adhesive material may peel off. Further, since the skin adhesive layer in the peripheral part is thin, the adhesive power thereof to skin in the peripheral part may lower as compared with that in the middle part.

In particular, in an adhesive patch that contains a drug liquid at room temperature, not only cold flow of the adhesive layer components but also a phenomenon of drug oozing from the adhesive layer during long-term storage occur, whereby the drug content in the adhesive patch may lower to cause a risk of drug efficacy reduction.

As another case of developing an adhesive patch, Patent Reference 2 relates to an adhesive patch-containing package bag in which the adhesive patch containing bisoprolol or a salt thereof in the adhesive layer thereof can be stored stably, and it discloses that, when the relative humidity inside the package bag is at most 25%, then the stability of bisoprolol or a salt thereof becomes excellent. However, the patent reference does not describe anything relating to oozing of bisoprolol or a salt thereof in the package bag and relating to the influence of cold flow of the adhesive layer component on the stability, the handleability and the adhesiveness of the adhesive patch, and much more nothing is investigated therein relating to the shape of the adhesive patch for solving the problems.

CITATION LIST

Patent References

Patent Reference 1: JP-A-2000-37413
Patent Reference 2: WO 2005/072716

SUMMARY OF THE INVENTION

Problems that the Invention is to Solve

The present invention has been made in consideration of the above-mentioned situation and is intended to provide an adhesive patch which effectively inhibits cold flow during storage, or that is, the occurrence of oozing or sticking out of the adhesive layer component from the exposed area of the adhesive layer of the adhesive patch as well as the occurrence of oozing of a drug from the adhesive layer to thereby prevent the reduction in drug content.

Means for Solving the Problems

As a result of assiduous investigations made for solving the above-mentioned problems, the inventors have found the followings. In an adhesive patch containing a drug excluding bisoprolol, when the support, the release liner and the adhesive layer constituting the adhesive patch each are formed to have a rectangular planar shape while the entire adhesive patch is formed to have a rectangular planar shape, and the adhesive patch is formed to have a protrudent part on the support-side surface thereof at a corner of the adhesive patch, and further when the adhesive patch is formed to have a middle part having a rectangular planar shape and a peripheral part in which the thickness of the adhesive patch is smaller than the thickness of the adhesive patch in the middle part while the protrudent part is formed at a corner of the middle part, and in case where the release liner is formed to have a split part and when the split part does not traverse the protrudent part of the corner, then during storage of the adhesive patch in a package, the opportunity for the exposed part of the adhesive layer of the adhesive patch to be in contact with the inner surface of the package can be reduced, and therefore, the drug and the other adhesive layer components can be prevented from oozing out or sticking out from the exposed part in the package. On the basis of these findings, the inventors have completed the present invention.

Namely, the present invention relates to the following [1] to [7].

[1] An adhesive patch comprising a support, an adhesive layer containing a drug excluding bisoprolol and arranged on at least one side of the support, and a release liner arranged on a side of the adhesive layer opposite to the side thereof on which the support is arranged,
wherein the support, the release liner and the adhesive layer each have a rectangular planar shape and the adhesive patch as a whole has a rectangular planar shape, and
wherein, at a corner of the adhesive patch, the adhesive patch comprises a protrudent part on a support-side surface thereof.

[2] The adhesive patch according to [1], wherein the adhesive patch comprises a peripheral part and a middle part having a rectangular planar shape, and wherein a thickness of the adhesive patch in the peripheral part is smaller than a thickness of the adhesive patch in the middle part, and the protrudent part is positioned at a corner of the middle part.

[3] The adhesive patch according to [1], wherein the adhesive patch comprises at least two protrudent parts and comprises, between said adjacent protrudent parts, a belt-like connecting built-up part in which a thickness of the adhesive patch is smaller than a thickness of the adhesive patch in the protrudent parts.

[4] The adhesive patch according to [1], wherein the protrudent part has a planar shape which is triangular, trapezoidal, crescent or semicircular.

[5] The adhesive patch according to [1], wherein the release liner comprises a split part that does not traverse the protrudent part.

[6] The adhesive patch according to [1], wherein the adhesive layer contains an organic liquid component.

[7] The adhesive patch according to [1], wherein the adhesive layer is not crosslinked.

Advantage of the Invention

According to the invention, in storing the adhesive patch in a package, the opportunity for the exposed part of the adhesive layer of the adhesive patch to be in contact with the inner surface of the package can be reduced. Consequently, even when the drug and the other adhesive layer components have oozed out or stuck out from the exposed part of the adhesive patch in the package, the adhesive patch can still be prevented from adhering to the inner surface of the package, and therefore the content of the drug in the adhesive patch can be prevented from reducing and the adhesive patch can be readily taken out from the package. In addition, during wear to skin, the opportunity for the edges of the adhesive patch to be rubbed against clothes and others can be reduced, and therefore it is possible to obtain an adhesive patch where the edges thereof hardly peel off, the adhesive strength to skin is sufficient and peeling from the skin surface rarely occurs.

BRIEF DESCRIPTION OF THE DRAWINGS

FIG. 1 is a schematic plan view of the adhesive patch of Example 1 of the invention.

FIG. 2(a) is a schematic cross-sectional view along I-I of the adhesive patch of FIG. 1; FIG. 2(b) is a schematic cross-sectional view along II-II of the adhesive patch of FIG. 1.

FIG. 3 is a schematic plan view of the adhesive patch of Example 2 of the invention.

FIG. 4(a) is a schematic cross-sectional view along I-I of the adhesive patch of FIG. 3; FIG. 4(b) is a schematic cross-sectional view along II-II of the adhesive patch of FIG. 3.

FIG. 5 is a schematic plan view of the adhesive patch of Comparative Example 2 of the invention.

FIG. 6(a) is a schematic cross-sectional view along I-I of the adhesive patch of FIG. 5; FIG. 6(b) is a schematic cross-sectional view along II-II of the adhesive patch of FIG. 5.

MODE FOR CARRYING OUT THE INVENTION

Figure 1:
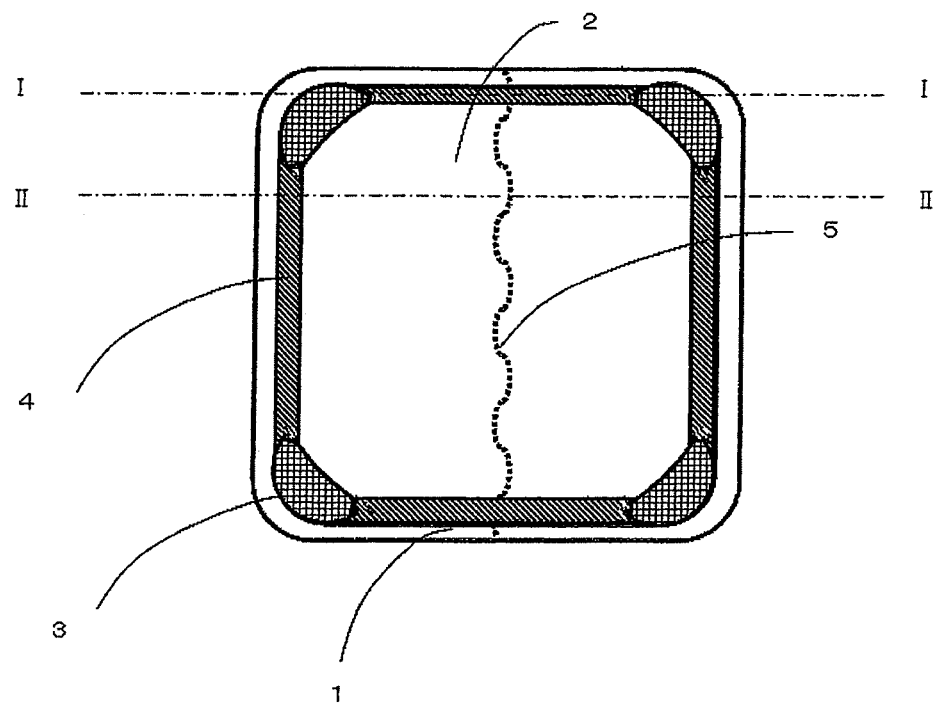
[FIG. 1]

The adhesive patch of the invention comprises a support, an adhesive layer containing a drug excluding bisoprolol and arranged on at least one side of the support, and a release liner arranged on a side of the adhesive layer opposite to the side thereof on which the support is arranged. The edges of the adhesive layer, more concretely, the side edges thereof are exposed out. The adhesive patch of the invention may be provided in any form of a matrix-type or reservoir-type, as a transdermal adhesive patch. Various dosage forms are employable here, including a patch-type form, an adhesive tape-type form, a sheet-type form, etc.

The support, the release liner and the adhesive layer each are formed to have a rectangular planar shape and the entire adhesive patch is formed to have a rectangular planar shape. In addition, the adhesive patch of the invention is formed to have a protrudent part on the support-side surface thereof at a corner thereof. The term "rectangle (rectangular)" as referred to in this description is meant to include a case where the corner is not rounded and also a case where the corner is somewhat rounded. In this case, the outline of the rectangle is composed of a rounded curve part and a linear part. The term "somewhat rounded" as referred to herein means that the ratio of the total length of the curve part to the total length of the linear part falls preferably within a range of from 0.1% to 40%, more preferably from 0.5% to 30%. In the invention, preferably, the adhesive patch has a rectangular planar shape having somewhat rounded corner, from the viewpoint of protecting the inner surface of package or the skin surface from being damaged or injured by the corner of the adhesive patch and from the viewpoint of protecting clothes from being getting stuck with it. The protrudent part provided on the support-side surface is considered to fulfill the function as a pillar to press and support the package material inside the package. Positioning the protrudent part at the corner of the adhesive patch realizes the structure where the protrudent part of the adhesive patch can efficiently support the entire adhesive patch, and enables the protrudent part to more effectively exhibit the pillar effect.

The above-mentioned protrudent part in the invention is formed on the support-side surface at the corner of the adhesive patch. One protrudent part but preferably multiple protrudent parts are formed, and more preferably, the protrudent parts are formed at respective corners. The wording "at corner" in this description is meant to include not only the presence of the protrudent part to be abut with the corner of the rectangular adhesive patch but also the presence of the protrudent part in the vicinity of the corner. The wording "in the vicinity of" as referred to herein means that the narrowest distance between the outline of the corner and the outline of the protrudent part, or that is, the distance in the narrowest site between the contoured part of the corner and the contoured part of the protrudent part is small. In the adhesive patch of the invention, the distance is preferably from 0.29 mm to 5 mm. The planar shape of the protrudent part includes a triangular shape, a trapezoidal shape, a crescent shape, a semicircular shape, etc. In the invention, these shapes include distorted ones and those having rounded corners. The "crescent shape" as referred to herein means a shape surrounded by a small arc having a small radius and a large arc having a large radius; the "semicircular shape" means a shape surrounded by a semicircle and its diameter. In the adhesive patch of the invention, the protrudent part on the support-side surface at the corner may be formed, for example, by thickening the support at the site thereof corresponding to the protrudent part and/or by thickening the adhesive layer at the site thereof corresponding to the protrudent part. In the latter case, the thickness of the support and that of the release liner are substantially uniform. In case where the thickness of the central part of the adhesive patch, or that is, the thickness of the site at which the diagonal lines of the rectangle cross each other is taken as 100%, the thickness of the adhesive patch at the protrudent part thereof is preferably from 110% to 300%, more preferably from 120% to 250%. The "thickness of the adhesive patch" is the total thickness of the support, the adhesive layer and the release liner constituting the adhesive patch.

Regarding the size of the protrudent part in the adhesive patch of the invention, preferably, the occupied area ratio of the protrudent part is from 2% to 90% or so of the entire surface of the support, more preferably from 2% to 85% or so. In case where the size of the protrudent part is such that the occupied area ratio thereof is less than 2%, and when the adhesive patch is stored in a package, the protrudent part could not fully support the inner surface of the package and the pillar effect of the protrudent part could not be expected. On the other hand, when the size of the protrudent part is such that the occupied area thereof is more than 90%, then the necessary amount of the adhesive layer may increase and therefore the adhesive patch may be uneconomical.

In one preferred embodiment of the adhesive patch of the invention, the adhesive patch includes a middle part having a rectangular planar shape and having a predetermined thickness of the adhesive patch, and also includes a peripheral part in which the thickness of the adhesive patch is smaller than the thickness of the adhesive patch in the middle part, and the protrudent part to be provided on the support-side surface is positioned at the corner of the middle part. In case where the adhesive patch has a middle part, the thickness of the adhesive patch in the middle part means the thickness of the above-mentioned central part of the adhesive patch. When the thickness of the adhesive patch in the peripheral part, especially the thickness of the adhesive layer therein is reduced, then the opportunity for the side edges of the adhesive patch to be in contact with the inner surface of package can be reduced, and the drug and other adhesive layer components can be prevented from oozing out or sticking out from the exposed area of the adhesive layer of the adhesive patch. Accordingly, in accordance with the adhesive patch of the invention, the reduction in the content of the drug during storage can be prevented and the adhesive patch can be readily taken out of the package.

Further, in the above-mentioned embodiment, even when the adhesive power of the peripheral part could be reduced by reducing the thickness of the adhesive layer in the peripheral part of the adhesive patch, the protrudent part in which the thickness of the adhesive layer is kept large is provided at the corner of the adhesive patch and, as a result, while kept stuck to skin, the adhesive power to the skin of the adhesive layer can be compensated at the corner of the peripheral part that could be the start point in peeling from the skin, and accordingly, the adhesive patch can be prevented from peeling away from the skin.

The planar shape of the peripheral part is preferably a belt-like one having a width of from 0.29 mm to 5 mm, more preferably from 0.29 mm to 3.5 mm. The width of the peripheral part falling within the above range makes it possible to more effectively prevent the drug and the other adhesive layer components from oozing out of or sticking out from the exposed area of the adhesive layer of the adhesive patch, and also makes it possible to more effectively prevent the adhesive power of the peripheral part of the adhesive patch from reducing. For sufficiently exhibiting the effect of the invention, preferably, the belt-like part is provided on every peripheral side of the adhesive patch.

In the adhesive patch mentioned above, the thickness in the peripheral part of the adhesive patch is preferably at least 1.5 µm from the viewpoint of securing the minimal adhesive power thereof to skin. On the other hand, the thickness in the middle part of the adhesive patch is, for example, from 50 µm to 5000 µm, preferably from 150 µm to 4000 µm. Falling within the above-mentioned ranges, the adhesive power to skin of the adhesive patch can be more effectively prevented from lowering, and in addition, since the adhesive layer can thereby retain the shape thereof with ease, the drug and other adhesive layer components can be more effectively prevented from oozing out of or sticking out from the exposed area of the adhesive layer of the adhesive patch. Preferably, the difference between the thickness of the adhesive patch in the middle part and the thickness of the adhesive patch in the peripheral part is from 20 µm to 2000 µm. In the above-mentioned case, the opportunity for the edges of the adhesive patch to be rubbed against the package or clothes can be reduced, and also the adhesive layer in the middle part can be given a necessary adhesive power.

The adhesive patch of the invention has a substantially planar flat shape and, as described above, the planar shape thereof is rectangular. Preferably, the length of one side of the adhesive patch is from 10 mm to 100 mm, more preferably from 15 mm to 80 mm. Regarding the wording "length of one side" as referred to herein, in case where the corners of the adhesive patch are rounded, such a rounded adhesive patch is converted into the corresponding, completely rectangular shape with no rounded corner and the length indicates the length of one side of the rectangular shape.

Preferably, the adhesive patch of the invention includes at least two protrudent parts. Also preferably, the adhesive patch includes, between the adjacent protrudent parts therein, a connecting built-up part in which the thickness of the adhesive patch is smaller than the thickness of the adhesive patch in the protrudent parts. Having the connecting built-up part, the adhesive patch can be well caught by the fingers when taken out of the package, and therefore the adhesive patch can be more readily taken out of the package. The thickness of the adhesive patch in the connecting built-up part is preferably from 105% to 250%, more preferably from 110% to 200%, relative to the thickness of the adhesive patch in the central part, 100%. The wording "adjacent" means that the two protrudent parts are in a relation where they are provided along one side of the adhesive patch.

Not specifically defined, the planar shape of the connecting built-up part is preferably a belt-like shape having a width of from 0.5 mm to 3 mm or so. The connecting built-up part can be formed by prolonging the pressing time or by increasing the pressure or the temperature in forming by pressing the peripheral part of the adhesive patch or by repeating twice or more the pressing step, as described below.

In the adhesive patch of the invention, the release liner may have a split part. In this case, the split part is so provided as not to traverse the protrudent part provided at the corner of the adhesive patch. Making the release liner have a split part, the adhesive layer can be exposed out at the split part. However, the split part is so provided as not to traverse the above-mentioned protrudent part and therefore the split part can be prevented from being given an external load from the outside of the package, and accordingly, the adhesive layer component can be prevented from oozing out or sticking out through the split part. In addition, while the adhesive patch is stored in a package, the pressure to be given to the split part from the package can be effectively reduced owing to the pillar effect of the protrudent part of the adhesive patch, and therefore the drug and other adhesive layer components can be prevented from oozing out or sticking out through the split part. As a result, the adhesive patch can be readily taken out of the package and the content of the drug can be prevented from reducing.

The split part of the release liner is formed by forming a cutting line on the surface of the release liner opposite to the contact surface with the adhesive layer. The form of the cutting line may be a linear, curved or waved one or may also be a combination of those forms. The cutting line may be either a solid line or a broken line or may also be a combination of those lines. Having such a split part, the release liner can be readily removed in use of the adhesive patch.

Not specifically defined, the support for use in the adhesive patch of the invention is preferably formed of a material through which components such as the drug contained in the adhesive layer do not penetrate to be lost from the back of the support, thereby causing the reduction in the content of those components, or that is, formed of a material impervious to the components contained in the adhesive layer.

The support usable in the adhesive patch of the invention includes a single film of polyester resins such as polyethylene terephthalate, etc.; polyamide resins such as nylon, etc.; olefinic resins such as polyethylene, polypropylene, etc.; vinylic resins such as ethylene-vinyl acetate copolymer, polyvinyl chloride, polyvinylidene chloride, ionomer resin, etc.; acrylic resins such as ethylene-ethyl acrylate copolymer, etc.; fluorocarbon resins such as polytetrafluoroethylene, etc.; metal foil or the like, and a laminate film of these. The thickness of the support is generally from 10 µm to 200 µm, preferably from 15 µm to 150 µm, more preferably from 20 µm to 100 µm. When the thickness of the support is at least 10 µm, then the adhesive layer components having oozed out or stuck out from the exposed area of the adhesive layer of the adhesive patch can be favorably prevented from running to the surface on the opposite side to the adhesive layer. On the other hand, when the thickness of the support is more than 200 µm, then the adhesive patch may feel rough when stuck to skin.

For enhancing the adhesiveness (anchorability) between the support and the adhesive layer, preferably, the support is a laminate film of a nonporous film formed of the above-mentioned material and a porous film, in which the adhesive layer is formed on the side of the porous film. Not specifically defined, the porous film may be any one capable of enhancing the anchorability between the support and the adhesive layer, including, for example, paper, woven fabric, nonwoven fabric, mechanically-perforated film, etc. Especially preferred are paper, woven fabric and nonwoven fabric. The thickness of the porous film is preferably from 10 µm to 100 µm in consideration of the anchorability improvement and the flexibility of the adhesive layer. In case where woven fabric or nonwoven fabric is employed as the porous film, its unit weight is preferably from 3 $g/m^2$ to 50 $g/m^2$, more preferably from 5 $g/m^2$ to 30 $g/m^2$ from the viewpoint of enhancing the anchorability.

Of the above-mentioned support, the most preferred support is a laminate film of a polyester-based resin film (preferably a polyethylene terephthalate film) having a thickness of from 1 µm to 45 µm and a polyester-based resin (preferably polyethylene terephthalate)-made nonwoven fabric having a thickness of from 10 µm to 100 µm and a unit weight of from 5 $g/m^2$ to 30 $g/m^2$.

Not specifically defined, the adhesive that constitutes the adhesive layer in the adhesive patch of the invention includes an acrylic adhesive including an acrylic copolymer; a rubbery adhesive such as styrene-diene-styrene block copolymer (e.g., styrene-isoprene-styrene block copolymer, styrene-butadiene-styrene block copolymer, etc.), polyisoprene, polyisobutylene, polybutadiene, etc.; a silicone-based adhesive such as silicone rubber, dimethylsiloxane base, diphenylsiloxane base, etc.; a vinyl ether-based adhesive such as polyvinyl methyl ether, polyvinyl ethyl ether, polyvinyl isobutyl ether, etc.; a vinyl ester-based adhesive such as vinyl acetate-ethylene copolymer, etc.; a polyester-based adhesive including a carboxylic acid component such as dimethyl terephthalate, dimethyl isophthalate, dimethyl phthalate or the like, and a polyalcohol component such as ethylene glycol or the like, etc. The adhesive layer formed of the adhesive may be crosslinked through physical crosslinking treatment of exposure to radiation such as UV irradiation, electron beam irradiation or the like, or through chemical crosslinking treatment with various crosslinking agents, or may also be a non-crosslinked adhesive layer with no crosslinking treatment applied thereto.

In particular, from the adhesive layer using a rubbery adhesive, the adhesive layer components tend to readily ooze out or stick out. Accordingly, the invention capable of effectively inhibiting the phenomenon is especially advantageous to the case where a rubbery adhesive is used as the adhesive to constitute the adhesive layer. For the same reason, the invention is also advantageous to the case of using a non-crosslinked adhesive layer.

The rubbery adhesive for use herein may be prepared by mixing the same components or different components that differ in point of the mean molecular weight, for the purpose of attaining suitable adhesive power and drug solubility. For example, a case of polyisobutylene is described. Preferred is a mixture of a high-molecular weight polyisobutylene having a viscosity-average molecular weight of from 1,800,000 to 5,500,000, a middle-molecular weight polyisobutylene having a viscosity-average molecular weight of from 40,000 to 85,000, and optionally a low-molecular weight polyisobutylene. The viscosity-average molecular weight as referred to in the invention is one calculated as follows: Using an Ubbelohde viscometer, the flow time at 20° C. of the polymer through a capillary is reckoned, and the Staudinger index ($J_0$) is derived from it according to the following Schulz-Blaschke formula (formula 1), and the value $J_0$ is introduced into the following Mark-Houwink-Sakurada formula (formula 2) to calculate the value.

[Numerical Formula 1]

$$J_0 = \eta_{sp}/c(1+A\eta_{sp}) \quad (1)$$

In the above formula, $\eta_{sp} = t/t_0 - 1$, t: flow time of the solution (according to the Hagenbach-Couette compensation formula), $t_0$: flow time of the solvent (according to the Hagenbach-Couette compensation formula), c: concentration of the solution (g/cm³), A: constant number specific to the polymer solution.

[Numerical Formula 2]

$$J_0 = kMv^\alpha \quad (2)$$

In the above formula, Mv is a viscosity-average molecular weight, and k and α each are a constant number specific to the polymer.

For polyisobutylene, A=0.31, k=3.06×10⁻², and α=0.65 in the above-mentioned formula 1 and formula 2, and the Mv value can be calculated from the $J_0$ value.

In case where polyisobutylene is used as the adhesive, a high-molecular weight polyisobutylene is compounded generally in a ratio of from 10% by weight to 80% by weight, preferably from 10% by weight to 50% by weight, a middle-molecular weight polyisobutylene is generally in a ratio of from 0% by weight to 90% by weight, preferably from 10% by weight to 80% by weight, and a low-molecular weight polyisobutylene is generally in a ratio of from 0% by weight to 80% by weight, preferably from 0% by weight to 60% by weight.

For giving suitable tackiness thereto, the adhesive layer may contain, for example, a tackifier such as a rosin-based resin, a polyterpene resin, a chroman-indene resin, a petroleum-based resin, a terpene-phenolic resin, xylene resin or the like. One type alone or two or more different types of these may be used here. Examples of the petroleum-based resin include aliphatic (C5-based) petroleum resin, aromatic (C9-based) petroleum resin, copolymer-type (C5-C9-based) petroleum resin, alicyclic saturated hydrocarbon resin obtained through partial hydrogenation or complete hydrogenation of aromatic (C9-based) petroleum resin, etc. The alicyclic saturated hydrocarbon resin is preferably one having a softening point, as measured according to a ring-and-ball method, of from 90° C. to 150° C. The tackifier may be compounded in the adhesive layer in a ratio of, for example, from 10% by weight to 40% by weight from the viewpoint of the ability thereof to impart suitable tackiness to the layer and of the effect to the amount thereof.

The adhesive layer may contain an organic liquid component miscible with the adhesive therein. The organic liquid component can plasticize the adhesive layer and can impart a soft feel to the layer. As a result, in case where an adhesive such as the above-mentioned acrylic adhesive or the rubbery adhesive is used as the adhesive to constitute the adhesive layer, the pain or the skin irritation to be caused by the adhesive power to skin of the adhesive patch can be reduced in peeling the adhesive patch from skin. Accordingly, any organic liquid component having a plasticizing effect may be used here with no specific limitation. From the viewpoint of enhancing the transdermal absorbability for the drug, preferred is use of those having an absorption-promoting effect.

In the invention, the organic liquid component preferably compounded in the adhesive layer includes vegetable oils such as olive oil, castor oil, palm oil, etc.; animal oils and fats such as liquid lanolin, etc.; organic solvents such as dimethyldecyl sulfoxide, methyloctyl sulfoxide, dimethyl sulfoxide, dimethylformamide, dimethylacetamide, dimethyllaurylamide, methylpyrrolidone, dodecylpyrrolidone, etc.; surfactants such as polyoxyethylene sorbitan fatty acid ester, sorbitan fatty acid ester, polyoxyethylene fatty acid ester, etc.; plasticizers such as diisopropyl adipate, phthalate, diethyl sebacate, etc.; hydrocarbons such as squalene, liquid paraffin, etc.; fatty acid alkyl esters such as ethyl oleate, isopropyl palmitate, octyl palmitate, isopropyl myristate, isotridecyl myristate, ethyl laurate, etc.; polyalcohol fatty acid esters such as glycerin fatty acid ester, propylene glycol fatty acid ester, etc.; ethoxylated stearyl alcohol; pyrrolidonecarboxylic acid alkyl esters; as well as long-chain aliphatic alcohols including linear aliphatic alcohols such as 1-dodecanol, 1-tetradecanol, 1-hexadecanol, etc., and branched aliphatic alcohols such as 2-hexyl-1-decanol, 2-octyl-1-dodecanol, 2-hexyl-1-tetradecanol, etc. One alone or two or more different types of these may be used here either singly or as combined. The organic liquid component may contain, as the constitutive ingredient thereof, any other organic component not liquid at room temperature (25° C.) so far as the component is liquid at room temperature (25° C.) as a whole.

The organic liquid component may be compounded in the adhesive layer preferably in a ratio of from 10% by weight to 60% by weight, more preferably from 15% by weight to 60% by weight, most preferably from 20% by weight to 60% by weight, relative to the total weight of the adhesive layer. In case where an adhesive layer contains an organic liquid component in a ratio of at least 10% by weight, the adhesive layer can readily plasticize and the adhesive layer components tend to often ooze out or stick out. Accordingly, the invention is advantageous to the case, as effectively inhibiting the phenomenon. In case where the organic liquid component is compounded in a ratio of more than 60% by weight, then the adhesive layer could hardly retain the constant shape thereof in some cases.

In the adhesive patch of the invention, the adhesive layer contains a drug except bisoprolol. Not specifically defined, the drug may be any one except bisoprolol, and may be any of systemic drugs or local-acting drugs. Preferred are transdermal drugs that are administrable to mammals including humans via the skin thereof. Concretely, for example, the drugs of the type include systemic anesthetics, antipsychotics, antidepressants, mood stabilizers, psychostimulants, narcotics, anxiolytics, antiepileptic drugs, migraine medications, antiemetics, anti-vertigenous drugs, local anesthetics, muscle relaxants, autonomic agents, antispasmodics, Parkinson disease remedies, corticosteroids, nonsteroidal antiinflammatory drugs, analgesic-antipyretics, antirheumatic drugs, antihistamines, antiallergics, cardiotonics, antiarrhythmics, diuretics, antihypertensives, vasoconstrictors, vasodilators, angina remedies, respiratory stimulants, bronchodilators, bronchial asthma remedies, antitussives, expectorants, hormone preparations, hematinics, hemostats, antithrombotic drugs, gout hyperuricemic remedies, diabetes remedies, hypolipidemic drugs, antineoplastics, immunosuppressants, antimicrobials, chemotherapeutics, antifungals, antivirals, antiparasitics, narcotics, stop smoking aids, etc. The adhesive patch of the invention may contain the drug except bisoprolol as a free form or as a salt with an acid or a base. The salt of the drug includes alkali metal salts such as sodium salts, potassium salts, etc.; alkaline earth metal salts such as magnesium salts, calcium salts, etc.; inorganic acid salts such as hydrochlorides, nitrates, sulfates, etc.; organic acid salts such as acetates, citrates, fumarates, maleates, etc.; salts with inorganic bases such as ammonium salts, etc.; salts with organic bases such as triethanolamine salts, pyridine salts, arginine salts, etc. The drugs can be produced according to per-se known production methods.

The content of the drug excluding bisoprolol is not specifically defined so far as it falls within a range capable of presenting the pharmaceutical effect thereof but not detracting from the adhesiveness or other properties of the adhesive layer. Preferably, it is contained in the adhesive layer in a ratio of from 0.1% by weight to 60% by weight, more preferably from 0.5% by weight to 40% by weight. When the content of the drug is less than 0.1% by weight, then the therapeutic efficacy would not be sufficient in some cases. When more than 60% by weight, there may occur skin irritation; and since the therapeutic efficacy is limited, use of such a large amount would be economically disadvantageous.

Not specifically defined, the release liner includes glassine paper, polyethylene, polypropylene, polyesters such as polyethylene terephthalate, etc., polystyrene, aluminium film, foamed polyethylene film, foamed polypropylene film, etc.; as well as laminates selected from these, silicone-processed or embossed products of these, etc. The thickness of the release liner is generally from 10 µm to 200 µm, preferably from 25 µm to 100 µm.

Among the release liners mentioned above, preferred are those formed of a polyester (especially, polyethylene terephthalate) resin from the viewpoint of the barrier property and the cost thereof. In particular, in this case, the thickness of the liner is preferably from 25 µm to 100 µm or so from the viewpoint of the handleability thereof.

Preferably, the release liner is processed for releasability-enhancing treatment on the interface thereof with the adhesive layer, in order that the release liner can be readily released from the adhesive layer. The releasability-enhancing treatment may be attained according to known methods. For example, there may be mentioned a treatment of forming a releasability-enhancing layer according to a coating method of bar coating, gravure coating or the like using a releasing agent that includes a curable silicone resin as the main ingredient thereof. The thickness of the releasability-enhancing layer is preferably from 0.01 µm to 5 µm from the viewpoint of securing the releasability and the uniformity of the coating layer. The thickness of the release liner having a releasability-enhancing layer formed thereon is generally from 10 µm to 200 µm, preferably from 25 µm to 100 µm from the viewpoint of the handleability of the liner.

In the adhesive patch of the invention, the release liner may be formed to have an extending part that extends outside from the body of the adhesive patch (laminate of the adhesive layer containing a drug excluding bisoprolol and the support). When the adhesive patch is packed in a package, the extending part reduces the opportunity for the edges of the adhesive patch body to be brought into contact with the inner surface of the package; and therefore, even when the adhesive layer components ooze out or stick out from the exposed area of the adhesive layer at the edge of the adhesive patch, they can be prevented from adhering to the inner surface of the package so that the adhesive patch could hardly be taken out of the package. In view of the effect, preferably, the release liner has such an extended part at least partly in the peripheral part of the adhesive patch body of the invention, more preferably has the extended part in the entire peripheral part thereof. The length of the extending part of the release liner is preferably from 0.5 mm to 10 mm or so, more preferably from 1 mm to 3 mm or so, taking the matter into consideration that the part can exhibit the above-mentioned effect not having any negative influence on packaging of adhesive patches.

The method for producing the adhesive patch of the invention is not specifically defined, for which, therefore herein employable is any known method generally employed in the art. For example, the above-mentioned adhesive, organic liquid component and others, and a drug excluding bisoprolol are dissolved or dispersed in a solvent in that order. Next, if desired, a crosslinking agent is added to the solution or the dispersion to prepare a composition for forming an adhesive layer. This is applied onto at least one side of a support and dried to form an adhesive layer thereon, and then a release liner is laminated under pressure thereonto to produce the adhesive patch. Alternatively, the solution or dispersion may be applied onto a release liner and dried to form the adhesive layer on the surface of the release liner, and thereafter a support is laminated under pressure onto the adhesive layer to produce the adhesive patch.

For coating with the composition to form an adhesive layer, for example, employable is any known coater such as a gravure roll coater, a reverse roll coater, a kiss roll coater, a dip roll coater, a bar coater, a knife coater, a spray coater, etc. From the viewpoint of accelerating the crosslinking reaction and enhancing the production efficiency, preferably, the composition is dried under heat. Depending on the type of the support to be coated with the composition, for example, a drying temperature of approximately from 40° C. to 150° C. or so may be employed here.

After the adhesive patch has been produced according to the method mentioned above, it may be aged at a temperature not lower than room temperature for the purpose of completing the crosslinking reaction or for enhancing the anchorability between the adhesive layer and the support. The aging temperature is generally within a range of from 25° C. to 80° C., preferably within a range of from 40° C. to 70° C.

In the adhesive patch of the invention, for the purpose of forming protrudent parts on the support-side surface at the corners thereof, any known method is employable. For example, employable is a method of thickening the support at the site thereof corresponding to the protrudent part, and/or a method of thickening the adhesive layer at the site thereof corresponding to the protrudent part.

For thickening the support at the site thereof corresponding to the protrudent part, any other member may be arranged at that site of the support, or the support itself may be formed to have the protrudent part. Similarly, for thickening the adhesive layer at the site thereof corresponding to the protrudent part, the adhesive layer-forming composition may be applied twice to that site, or an adhesive layer separately formed may be stuck to that site.

Next, the adhesive patch of another embodiment of the invention, which has a peripheral part and a middle part having a rectangular planar shape and in which the thickness of the adhesive patch in the peripheral part is smaller than the thickness of the adhesive patch in the middle part and the protrudent part is positioned at a corner of the middle part, can be produced, for example according to the method mentioned below.

As described above, an adhesive layer is formed on at least one side of a support and then a release liner is laminated thereon, or an adhesive layer is formed on one side of a release liner and then a support is laminated therein, thereby preparing an adhesive patch-blanking precursor sheet (hereinafter simply referred to as "precursor sheet"). The precursor sheet is arranged on a press bed in such a manner that the release liner thereof could face the press bed, and pressed for shaping against a heated press die having a predetermined shape, on the side of the support thereof. After thus pressed for shaping, the sheet is blanked at a predetermined blanking position. The predetermined shape of the press die is a shape capable of pressing at least the region corresponding to the rectangular peripheral part. Thus pressing the region corresponding to the peripheral part forms the peripheral part in which the thickness of the adhesive patch is smaller than that in the middle part. The predetermined blanking position is a position that outlines the profile of the adhesive patch in such a manner that the region corresponding to the rectangular peripheral part of the adhesive patch could be included in the adhesive patch. Further, the thus-blanked sheet is then pressed and heated against a heated press die, thereby forming therein a protrudent part at the corner of the middle part or further forming a built-up part at the site corresponding to the connecting part between the protrudent parts. The shape of the heated press die depends on the shape of the adhesive patch to be formed, and as one example thereof, there may be mentioned a planar shape as outlined by concentric two rectangles. For continuous production of adhesive patches, a blanking position to form arrays of adhesive patches is simulated on the precursor sheet, and the pressing and blanking may be continuously repeated to thereby efficiently produce adhesive patches from the precursor sheet.

In producing the adhesive patches of the invention according to the above-mentioned method, preferably, a heated press die is used in pressing. Pressing with a heated press die softens by heat the support adjacent to the pressed region, whereby the adhesive layer in the pressed region moves to the corners of the adhesive patch and to the connecting part between the formed protrudent parts to thereby promote the projection at the corners and the embossment of the connecting part. The protrudent part and the built-up part formed by the above can retain the shape thereof by cooling, for example, by spontaneous cooling or the like.

The temperature of the heated press die is preferably from 90° C. to 180° C., more preferably from 120° C. to 150° C. The pressure in pressing is preferably from $1\times10^4$ N/m$^2$ to $1\times10^9$ N/m$^2$, more preferably from $1\times10^6$ N/m$^2$ to $1\times10^8$ N/m$^2$. The pressing time is preferably from 0.05 seconds to 5 seconds, more preferably from 0.1 seconds to 1 second. For forming the connecting built-up part, the temperature of the press die varies depending on the thickness and the composition of the adhesive layer and on the shape, the thickness and the material of the support, but is preferably higher. For example, the temperature of the press die is from 110° C. to 180° C., the pressure in pressing is from $1\times10^6$ N/m$^2$ to $1\times10^8$ N/m$^2$, and the pressing time is from 0.05 seconds to 5 seconds. For efficiently forming the connecting built-up part, preferably, the temperature of the press bed is within a range of from 25° C. to 50° C. When the temperature of the press bed is controlled to fall within the above range, it may be considered that the adhesive layer can be prevented from having too much fluidity due to the influence thereon of the press die heated in pressing, and therefore, the above-mentioned shape of the adhesive patch can be thereby efficiently formed.

The distance between the press die and the press bed is preferably the total thickness of the support, the adhesive layer in the peripheral part and the release liner±10 μm or so.

The material of the press die for pressing is not specifically defined, but preferably the press die is an iron-made one. A stainless-made one would be distorted by heat and would be difficult to work. An aluminium-made one and a brass-made one are easy to work but may be poor in die durability, and would be therefore often unfavorable.

After the pressing, the blanking to give adhesive patches may be attained according to ordinary methods using a laser, a pressing blade or the like. Preferred is use of a pressing blade die set (male die and female die) as facilitating cutting dimension control and position alignment and as giving good cut edges.

In case where the release liner has an extending part, only the adhesive patch body is first blanked out, and then the release liner is blanked out, so that the extending part can be readily formed. The length of the extending part may be controlled by controlling the dimensional difference between the male die and the female die of the pressing blade die set. The split part of the release liner may be formed by half-cutting the middle part of the release liner with a die roll to thereby introduce a cutting line only into the release liner.

Preferably, the adhesive patch of the invention is packed in a package and stored as such. The package may be produced using a package material generally used for packaging of adhesive patches. The package material includes, for example, polyolefinic resin films such as polyethylene film, polypropylene film, polymethylpentene film, etc.; vinylic resin films such as polyvinyl chloride film, polyvinylidene chloride film, polyvinyl alcohol film, polystyrene film, polyacrylonitrile film, ionomer film, etc.; polyester-based resin films such as polyethylene terephthalate film, etc.; polyamide-based resin films such as nylon film, etc.; cellulosic resin films such as cellophane, etc.; polycarbonate resin films, and their laminate films, and further laminate films of these and aluminium. Packing the adhesive patch in the package formed of the package material as above, and sealed up according to a known method of heat sealing or the like.

EXAMPLES

The invention is described more concretely with reference to the following Examples and Comparative Examples; however, the invention is not limited by the following Examples.
<Preparation of Adhesive Layer Forming Composition A>

(i) 95 parts by weight of 2-ethylhexyl acrylate (by Toa Gosei), 5 parts by weight of acrylic acid (by Toa Gosei), 100 parts by weight of ethyl acetate and 0.2 parts by weight of benzoyl peroxide ("NYPER BW", by NOF) were reacted in a separable flask equipped with a reflux condenser, a stirrer, a thermometer, a dropping funnel and a nitrogen introducing duct, in a nitrogen atmosphere at 60° C. for 15 hours, to prepare an acrylic adhesive solution.

(ii) Relative to 40 parts by weight of the solid content of the acrylic adhesive solution, 40 parts by weight of isopropyl palmitate (by Croda Japan) as an organic liquid component and 20 parts by weight of isosorbide nitrate (by DKSH Japan) as a drug were mixed with the solution. Further, as a crosslinking agent, an isocyanate-based crosslinking agent ("CORONATE HL", by Nippon Polyurethane Industry) was mixed in the solution in a ratio of 0.05% by weight relative to the solid content of the acrylic adhesive solution, and ethyl acetate was further added thereto for viscosity control to prepare an adhesive layer forming composition A.

<Preparation of Adhesive Layer Forming Composition B>

A high-molecular weight polyisobutylene (viscosity-average molecular weight=$4 \times 10^6$, "OPPANOL B200", by BASF), a middle-molecular weight polyisobutylene (viscosity-average molecular weight=$8.5 \times 10^4$, "OPPANOL B15N", by BASF), as a tackifier, an alicyclic saturated hydrocarbon resin ("ARCON P-100", by Arakawa Chemical Industry, softening point (by ring-and-ball method)=$100 \pm 5°$ C.), as an organic liquid component, isopropyl palmitate (by Croda Japan), and as a drug, tulobuterol (by Sumitomo Chemical) were mixed in hexane in a ratio by weight of 15/20/25/30/10, and processed for viscosity control to prepare an adhesive layer forming composition B.

<Preparation of Adhesive Sheet A>

The adhesive layer forming composition A was applied onto the release face of a release liner (thickness 75 µm) formed of polyethylene terephthalate (hereinafter this may be referred to as "PET") in such a manner that the thickness of the adhesive layer after dried could be 200 µm, and then dried with a drier (100° C., 3 minutes), thereby forming an adhesive layer on the release liner. Next, as a support, a laminate of a PET-made film having a thickness of 3.5 µm and a PET-made nonwoven fabric having a thickness of about 35 µm and a unit weight of 12 g/m² (total thickness, about 40 µm) was stuck under pressure to the adhesive layer-formed face of the liner with the PET-made nonwoven fabric kept facing the adhesive layer, thereby preparing an adhesive sheet. The adhesive sheet was statically kept in a thermostatic chamber at 70° C. for 48 hours to thereby promote the crosslinking reaction of the adhesive layer. The release liner alone of the thus-prepared adhesive sheet was cut along a wavy line, thereby preparing an adhesive sheet A having a split part.

<Preparation of Adhesive Sheet B>

The adhesive layer forming composition B was applied onto the release face of a PET-made release liner (thickness 75 µm) in such a manner that the thickness of the adhesive layer after dried could be 200 µm, and then dried with a drier (70° C., 2 minutes), thereby forming an adhesive layer on the release liner. As a support, a laminate of a PET-made film having a thickness of 3.5 µm and a PET-made nonwoven fabric having a thickness of about 35 µm and a unit weight of 12 g/m² (total thickness, about 40 µm) was stuck under pressure to the adhesive layer-formed face of the liner with the PET-made nonwoven fabric kept facing the adhesive layer, thereby preparing an adhesive sheet. The release liner alone of the thus-prepared adhesive sheet was cut along a wavy line, thereby preparing an adhesive sheet B having a split part.

<Preparation of Adhesive Sheet C>

The adhesive layer forming composition A was applied onto the release face of a PET-made release liner (thickness 75 µm) in such a manner that the thickness of the adhesive layer after dried could be 180 µm, and then dried with a drier (100° C., 3 minutes), thereby producing a laminate A having the adhesive layer laminated on the release liner. A laminate of a PET-made film having a thickness of 3.5 µm and a PET-made nonwoven fabric having a thickness of about 35 µm and a unit weight of 12 g/m² (total thickness, about 40 µm) was used as a support, and the adhesive layer forming composition A was applied onto the PET-made nonwoven fabric side of the laminate in such a manner that the thickness of the adhesive layer after dried could be 60 µm and the width thereof could be 10 mm, and dried with a drier (100° C., 3 minutes), thereby producing a laminate B having the adhesive layer laminated on the support. The laminate A and the laminate B were stuck together under pressure in such a manner that the adhesive layer sides of the two could face each other, thereby producing an adhesive sheet. The adhesive sheet was statically kept in a thermostatic chamber at 70° C. for 48 hours to thereby promote the crosslinking reaction of the adhesive layer. The middle part of the release liner corresponding to the laminate B (thick part) of the prepared adhesive sheet was cut along a wavy line, thereby producing an adhesive sheet C having a split part.

<Preparation of Adhesive Sheet D>

The adhesive layer forming composition B was applied onto the release face of a PET-made release liner (thickness 75 µm) in such a manner that the thickness of the adhesive layer after dried could be 180 µm, and then dried with a drier (70° C., 2 minutes), thereby producing a laminate C having the adhesive layer laminated on the release liner. A laminate of a PET-made film having a thickness of 3.5 µm and a PET-made nonwoven fabric having a thickness of about 35 µm and a unit weight of 12 g/m² (total thickness, about 40 µm) was used as a support, and the adhesive layer forming composition B was applied onto the PET-made nonwoven fabric side of the laminate in such a manner that the thickness of the adhesive layer after dried could be 60 µm and the width thereof could be 10 mm, and dried with a drier (70° C., 2 minutes), thereby producing a laminate D having the adhesive layer laminated on the support. The laminate C and the laminate D were stuck together under pressure in such a manner that the adhesive layer sides of the two could face each other, thereby producing an adhesive sheet. The middle part of the release liner corresponding to the laminate D (thick part) of the prepared adhesive sheet was cut along a wavy line, thereby producing an adhesive sheet D having a split part.

<Production of Adhesive Patch>

Example 1

The adhesive sheet A was arranged on a press bed having a surface temperature of 30° C. Using a heated rectangular press die (outer dimension: 32 mm×32 mm, radius of the arc-curved part (hereinafter this is simply referred to as "R"): 5 mm, inner dimension: 28 mm×28 mm, R: 1 mm, made of iron), the support surface of the adhesive sheet A was heated under pressure (heating temperature: 150° C., press die pressure: $2 \times 10^7$ N/m², heating and pressing time; 0.3 seconds) in such a manner that the split part of the release liner could be nearly in the center of the adhesive patch. Using a pressing blade, the adhesive patch body and the release liner were together blanked out from the heated and pressed adhesive sheet A in such a manner that the heated and pressed region could correspond to the peripheral part of the adhesive patch to be obtained later, thereby producing an adhesive patch of Example 1.

Example 2

An adhesive patch of Example 2 was produced in the same manner as in Example 1, except that the heating and pressing conditions were changed to: a heating temperature of 100° C., a press die pressure of $2\times10^7$ N/m$^2$, and a heating and pressing time of 0.3 seconds.

Example 3

An adhesive patch of Example 3 was produced in the same manner as in Example 1, for which, however, the adhesive sheet B was used in place of the adhesive sheet A.

Example 4

An adhesive patch of Example 4 was produced in the same manner as in Example 2, for which, however, the adhesive sheet B was used in place of the adhesive sheet A.

Comparative Example 1

An adhesive patch of Comparative Example 1 was produced in the same manner as in Example 1, for which, however, the heating and pressing treatment with the press die was omitted.

Comparative Example 2

An adhesive patch of Comparative Example 2 was produced by blanking the adhesive sheet C to have a planar shape, like in Comparative Example 1.

Comparative Example 3

An adhesive patch of Comparative Example 3 was produced in the same manner as in Example 3, for which, however, the heating and pressing treatment with the press die was omitted.

Comparative Example 4

An adhesive patch of Comparative Example 4 was produced by blanking the adhesive sheet D to have a planar shape, like in Comparative Example 2.

<Packaging of Adhesive Patch>

The adhesive patch of Examples 1 and 2 and Comparative Examples 1 and 2 was sealed up and packaged in a package (outer dimension: 95 mm×95 mm, inner dimension: 85 mm×85 mm) formed of a package material of which the outer layer was a PET film having a thickness of 12 μm, the inner layer was a polyacrylonitrile-based resin film having a thickness of 30 μm and the center layer was aluminium having a thickness of 7 μm. The adhesive patch of Examples 3 and 4 and Comparative Examples 3 and 4 was sealed up and packaged in a package formed of the above-mentioned package material and having an outer dimension of 65 mm×65 mm and an inner dimension: 55 mm×55 mm.

Test Example 1

Shape Evaluation of Adhesive Patch

The planar shape of the adhesive patch of Examples 1 to 4 and Comparative Examples 1 to 4 was observed. In addition, the adhesive patch was frozen in liquid nitrogen and rapidly taken out, and cut with a trimming blade at low temperature in the vertical direction from the support (6) face. Using a digital microscope, the cut face was observed to measure each thickness (total thickness of the support (6), the adhesive layer (7) and the release liner (8)) in the peripheral part (1), the middle part (2), the protrudent part (3) and the connecting built-up part (4). At the same time, the width of the peripheral part (1) was measured. The results are shown in Table 1, and FIGS. 1 to 6.

TABLE 1

| Sample | Shape of Adhesive Patch | Protrudent part Position, Number, Shape | Protrudent part Occupied Area Ratio (%) | Protrudent part Thickness (μm) | Connecting Built-Up Part Thickness (μm) | Connecting Built-Up Part Width (mm) | Middle Part Thickness (μm) | Peripheral Part Thickness (μm) | Peripheral Part Width (mm) |
|---|---|---|---|---|---|---|---|---|---|
| Example 1 | Rectangle (30 mm square) R = 3 mm | at the corners of middle part, four, crescent shape | 16 | 520 | 400 | 1.5 | 310 | 120 | 2 |
| Example 2 | Rectangle (30 mm square) R = 3 mm | at the corners of middle part, four, crescent shape | 11 | 460 | — | — | 310 | 180 | 2 |
| Comparative Example 1 | Rectangle (30 mm square) R = 3mm | none | — | — | — | — | 310 | — | — |
| Comparative Example 2 | Rectangle (30 mm square) R = 3 mm | on the split part of release liner, belt-like (width 10 mm) | 34 | 340 | — | — | 280 | — | — |
| Example 3 | Rectangle (30 mm square) R = 3 mm | at the corners of middle part, four, crescent shape | 16 | 510 | 380 | 1.5 | 300 | 120 | 2 |
| Example 4 | Rectangle (30 mm square) R = 3 mm | at the corners of middle part, four, crescent shape | 11 | 460 | — | — | 300 | 180 | 2 |
| Comparative Example 3 | Rectangle (30 mm square) R = 3 mm | none | — | — | — | — | 300 | — | — |
| Comparative Example 4 | Rectangle (30 mm square) R = 3 mm | on the split part of release liner, belt-like (width 10 mm) | 34 | 340 | — | — | 280 | — | — |

* In the Table "crescent shape" means a crescent shape rounded at the corner.

Figure 2:
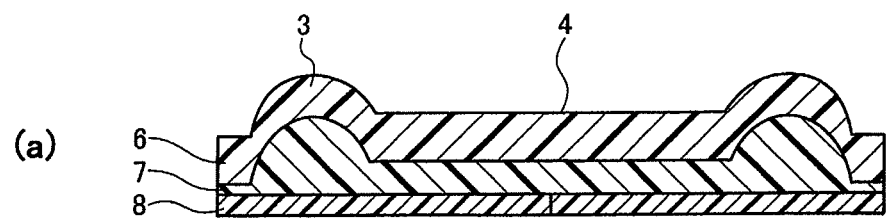
[FIG. 2]
Figure 2:
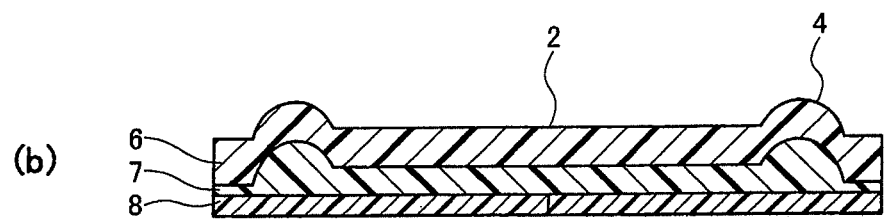

FIG. 1 schematically shows the planar shape of the adhesive patch of Example 1. FIGS. 2(a) and (b) each schematically show the profile of the cross section of the adhesive patch of Example 1, as cut from the support (6) surface in the vertical direction along the line I-I and the line II-II, respectively, in FIG. 1. As obvious from Table 1 and FIGS. 1 and 2, the adhesive patch of this Example had a peripheral part (1) having a width of 2 mm and a middle part (2) inside the peripheral part. The external shape of the adhesive patch is a rectangle (30 mm×30 mm) rounded at the corners thereof (R=3 mm), and in the outline thereof, the ratio of the total length of the curved parts to the total length of the linear parts was about 19.6%. Every planar shape of the support (6), the release liner (8) and the adhesive layer (7) was also a rectangle rounded at the corners, and the planar shape of the middle part (2) was also a rectangle rounded at the corners. At every corner thereof, the rectangular adhesive patch had a crescent protrudent part (3) rounded at the corner thereof, therefore having four such protrudent parts in total. Between the adjacent protrudent parts (3), the adhesive patch had a belt-like connecting built-up part (4) in which the thickness of the adhesive patch was smaller than the thickness of the adhesive patch in the protrudent part (3). Further, the split part (5) of the release liner was so arranged as not overlap with the four protrudent parts (3). The protrudent part (3) and the connecting built-up part (4) were formed by the change in the thickness of the adhesive layer (7) on the support (6)-side surface of the adhesive patch.

Figure 3:
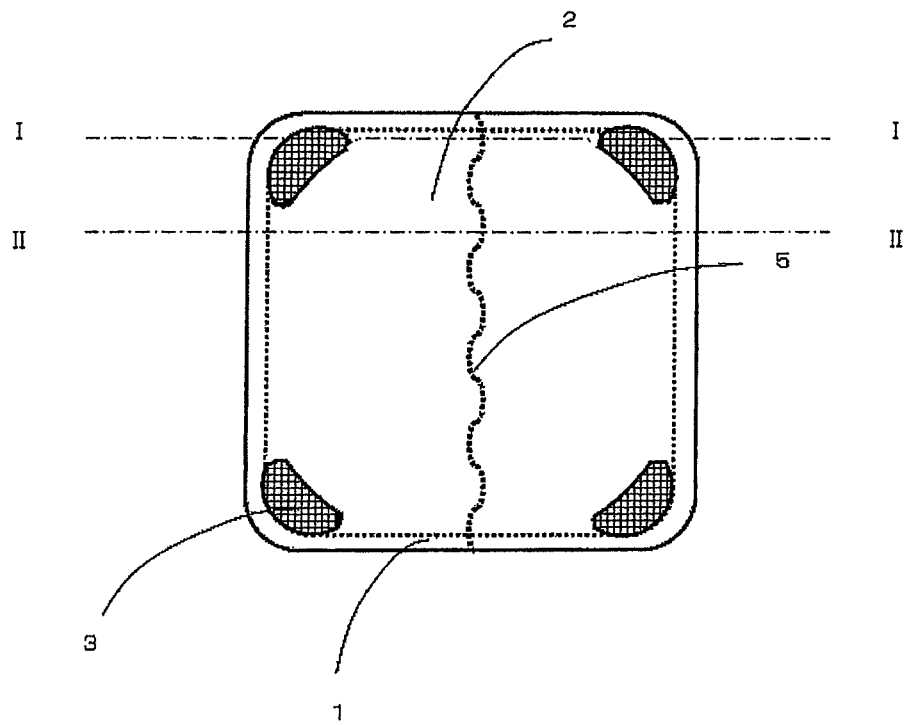
[FIG. 3]
Figure 4:
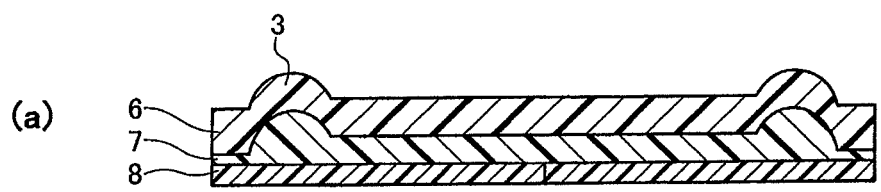
[FIG. 4]
Figure 4:
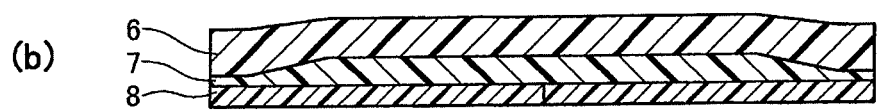

Next, FIG. 3 schematically shows the planar shape of the adhesive patch of Example 2. FIGS. 4(a) and (b) each schematically show the profile of the cross section of the adhesive patch of Example 2, as cut from the support (6) surface in the vertical direction along the line I-I and the line II-II, respectively, in FIG. 3. As obvious from Table 1 and FIGS. 3 and 4, the shape and the like of the adhesive patch of this Example was the same as the shape and the like of the adhesive patch of Example 1 except that the former did not have the belt-like connecting built-up part (4) between the adjacent protrudent parts (3).

On the other hand, as shown in Table 1, each external form of the adhesive patch and the like of Comparative Example 1 had a rectangular planar shape rounded at the corners thereof. However, the adhesive patch produced herein did not have the peripheral part (1) and the inner middle part (2) which the adhesive patch of Example 1 had, and in addition, the adhesive patch produced herein did not have the protrudent part (3) at the corner part of the rectangle thereof. In the outline of external form of the adhesive patch of this Comparative Example, the ratio of the total length of the curved parts to the total length of the linear parts was about 19.6%, and was on the same level as in the adhesive patch of Example 1.

Figure 5:
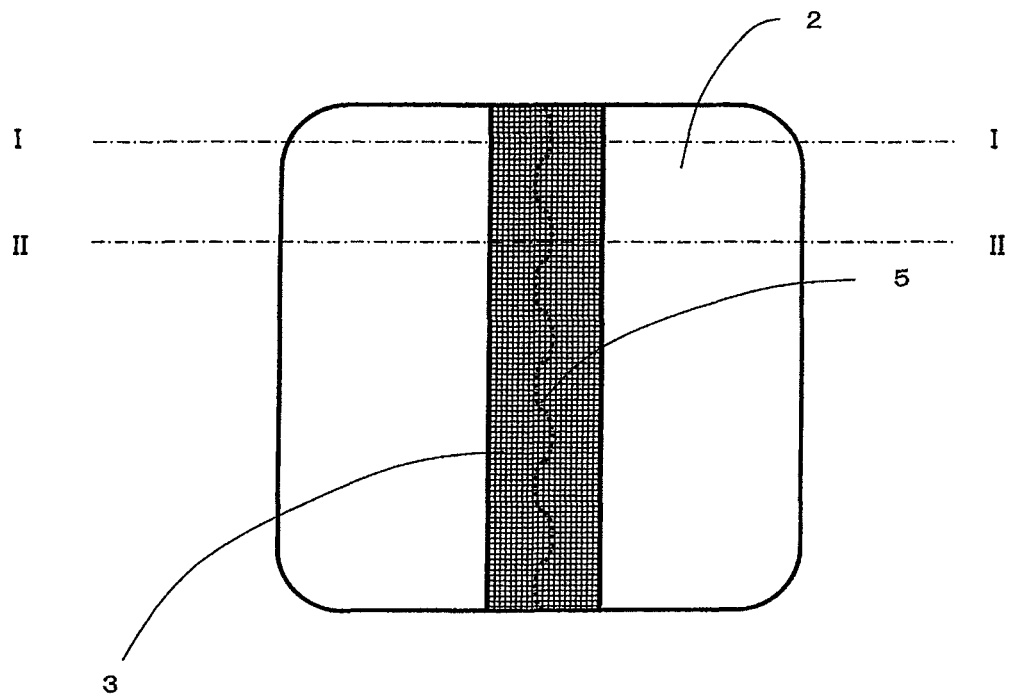
[FIG. 5]
Figure 6:
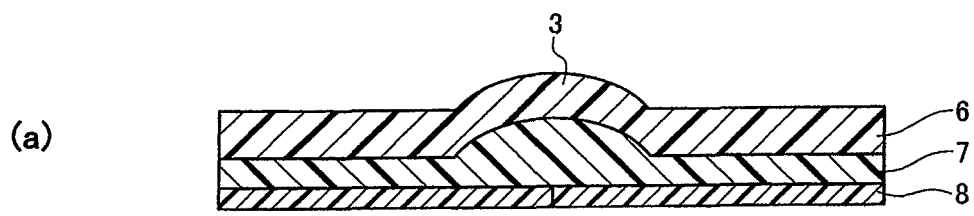
[FIG. 6]
Figure 6:
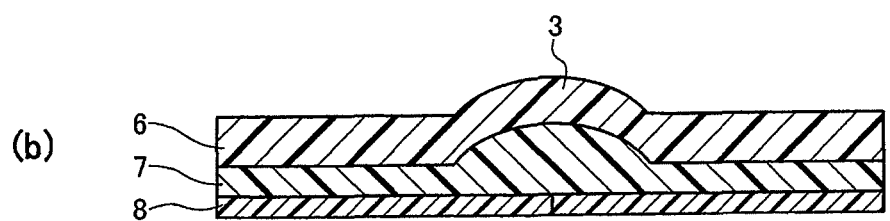

FIG. 5 schematically shows the planar shape of the adhesive patch of Comparative Example 2. FIGS. 6(a) and (b) each schematically show the profile of the cross section of the adhesive patch of Comparative Example 2, as cut from the support (6) surface in the vertical direction along the line I-I and the line II-II, respectively, in FIG. 5. As obvious from Table 1 and FIGS. 5 and 6, each external form of the adhesive patch and the like of Comparative Example 2 had a rectangular planar shape rounded at the corners thereof, and had the protrudent part (3) having a width of 10 mm, in which, however, the protrudent part (3) was arranged on the split part (5) of the release liner. In the outline of the of the external form of the adhesive patch of this Comparative Example, the ratio of the total length of the curved parts to the total length of the linear parts was about 19.6%, and was on the same level as in the adhesive patch of Example 1.

Next, as shown in Table 1, the shape and others of the adhesive patch of Example 3 were the same as the shape and others of the adhesive patch of Example 1; and the shape and others of the adhesive patch of Example 4 were the same as the shape and others of the adhesive patch of Example 2.

Also obvious from Table 1, like the adhesive patch of Comparative Example 1, the adhesive patch of Comparative Example 3 did not have the peripheral part (1), the inner middle part (2) and the protrudent parts (3) at the corners of the rectangle. Like the adhesive patch of Comparative Example 2, the adhesive patch of Comparative Example 4 had the protrudent part (3) having a width of 10 mm, in which, however, the protrudent part was arranged on the split part (5) of the release liner. In the outline of the of the external form of the adhesive patch of these Comparative Examples, the ratio of the total length of the curved parts to the total length of the linear parts was about 19.6%, and was on the same level as in the adhesive patch of Example 1.

Test Example 2

Evaluation of Amount of Drug Oozed from Adhesive Patch

The adhesive patch of Examples 1 to 4 and Comparative Examples 1 to 4 was stored at 60° C. for 1 month, and then in the package in which the adhesive patch had been packaged, the drug having adhered to the package material was extracted out with methanol and quantified through high-performance liquid chromatography (HPLC). The ratio of the amount of the drug having adhered to the package to the amount of the drug in the adhesive patch of Examples and Comparative Examples is shown in Table 2.

TABLE 2

| Sample | Amount of Drug Adhered to Package (μg/bag) | Ratio of Drug Adhered to Package to Drug Contained in Adhesive Patch (%) |
| --- | --- | --- |
| Example 1 | 68 | 0.2 |
| Example 2 | 123 | 0.4 |
| Comparative Example 1 | 514 | 1.6 |
| Comparative Example 2 | 826 | 2.8 |
| Example 3 | 14 | 0.1 |
| Example 4 | 22 | 0.1 |
| Comparative Example 3 | 90 | 0.5 |
| Comparative Example 4 | 123 | 0.7 |

Table 2 shows that, in the adhesive patches of Examples 1 and 2, the amount of isosorbide nitrate having adhered to the package was ¼ or less, as compared with that in the adhesive patches of Comparative Examples 1 and 2. Also in the adhesive patches of Examples 3 and 4, the amount of tulobuterol having adhered to the package was ⅕ or less of the amount thereof in the adhesive patches of Comparative Examples 3 and 4. In the adhesive patches of Comparative Examples 2 and 4, which had the protrudent part (3) on the split part (5), not only the drug oozing from the exposed area of the adhesive layer at the edge of the peripheral part of the adhesive patch but also the drug oozing from the exposed area of the adhesive layer at the split part (5) was remarkable, and therefore the ratio of the drug having adhered to the package was high. The results in Table 2 confirm that in the adhesive patches of the invention, not only the drug oozing from the exposed area of the adhesive layer at the edge of the peripheral part of the adhesive patch but also the drug oozing from the exposed area of the adhesive layer at the split part (5) can be favorably prevented.

Test Example 3

Evaluation of Easy Takeout of Adhesive Patch from Package

The adhesive patch of Examples 1 to 4 and Comparative Examples 1 to 4 was stored at 60° C. for 1 month, as packaged in a package. Afterwards, the package was opened by cutting two sides thereof with scissors. From the opened part, the adhesive patch was taken out by pinching the corner thereof, and evaluated for the easiness in taking out the adhesive patch from the package, according to the following evaluation criteria with from 1 to 5 evaluation points. The evaluation results are shown in Table 3.

<Evaluation Criteria>
5: Extremely easy to take out.
4: Slightly caught, but possible to take out.
3: Caught, but possible to take out.
2: Noticeably caught, but possible to take out.
1: The adhesive patch stuck to the package and was difficult to take out.

TABLE 3

| Sample | Easiness in Taking out of Adhesive Patch from Package |
| --- | --- |
| Example 1 | 5 |
| Example 2 | 4 |
| Comparative Example 1 | 1 |
| Comparative Example 2 | 1 |
| Example 3 | 5 |
| Example 4 | 4 |
| Comparative Example 3 | 1 |
| Comparative Example 4 | 1 |

As obvious from Table 3, the adhesive patches of Examples 1 to 4 were easy to take out from the package, but the adhesive patches of Comparative Examples 1 to 4 adhered to the inner surface of the package and were difficult to take out from the package. The adhesive patches of Examples 1 and 3 had the connecting built-up part (4), and were therefore easier to take out from the package than the adhesive patches of Examples 2 and 4 not having the connecting built-up part (4).

Test Example 4

Evaluation of Oozing Out or Sticking out of Adhesive Layer Components from the Exposed Area of the Adhesive Layer in the Split Part and the Peripheral Edge of Adhesive Patch The adhesive patch taken out from the package in Test Example 3 was visually checked for the state of oozing out or sticking out of the adhesive layer components from the exposed area of the adhesive layer in the split part (5) and in the peripheral edge of the adhesive patch, and evaluated according to the following evaluation criteria with from 1 to 5 evaluation points. The evaluation results are shown in Table 4.

<Evaluation Criteria>
5: In the exposed area of the adhesive layer in the split part and in the peripheral edge of the adhesive patch, no adhesive layer components oozed out or stuck out at all.
4: Of the whole length of the exposed area of the adhesive layer in the split part and in the peripheral edge of the adhesive patch, the adhesive layer components oozed out or stuck out in less than ¼.
3: Of the whole length of the exposed area of the adhesive layer in the split part and in the peripheral edge of the adhesive patch, the adhesive layer components oozed out or stuck out in from ¼ to less than ½.
2: Of the whole length of the exposed area of the adhesive layer in the split part and in the peripheral edge of the adhesive patch, the adhesive layer components oozed out or stuck out in from ½ to less than ¾.
1: Of the whole length of the exposed area of the adhesive layer in the split part and in the peripheral edge of the adhesive patch, the adhesive layer components oozed out or stuck out in ¾ or more.

TABLE 4

| | Oozing out or Sticking out of Adhesive Layer Components | |
| --- | --- | --- |
| Sample | Split Part | Peripheral Edge of Adhesive Patch |
| Example 1 | 5 | 5 |
| Example 2 | 5 | 4 |
| Comparative Example 1 | 2 | 1 |
| Comparative Example 2 | 1 | 1 |
| Example 3 | 5 | 5 |
| Example 4 | 5 | 4 |
| Comparative Example 3 | 3 | 1 |
| Comparative Example 4 | 2 | 1 |

As obvious from Table 4, in the adhesive patches of Examples 1 to 4, the adhesive layer components oozed out or stuck out little from the exposed area of the adhesive layer in the split part (5) and in the peripheral edge of the adhesive patch. On the other hand, in the adhesive patches of Comparative Examples 1 to 4, the adhesive layer components oozed out or stuck out noticeably from the exposed area of the adhesive layer and in the peripheral edge of the adhesive patch, and especially in the adhesive patches of Comparative Examples 2 and 4, the adhesive layer components oozed out or stuck out noticeably also from the exposed area of the adhesive layer in the split part (5) than in the adhesive patches of Comparative Examples 1 and 3.

While the invention has been described in detail and with reference to specific embodiments thereof, it will be apparent to one skilled in the art that various changes and modifications can be made therein without departing from the scope thereof. This application is based on Japanese patent application No. 2010-043100 filed Feb. 26, 2010, the entire contents thereof being hereby incorporated by reference.

Industrial Applicability

As described in detail hereinabove, according to the invention, there is provided an adhesive patch which contains a drug except bisoprolol and of which the drug and other adhesive layer components are favorably prevented from oozing out or sticking out from the exposed area of the adhesive layer such as the edge of the adhesive patch or the split part. As a result, when the adhesive patch is packed in a package and stored in the package for a long period of time, the adhesive patch is prevented from adhering to the inner face of the package and the content of the drug in the adhesive patch during storage is prevented from reducing. In addition, the invention provides an adhesive patch that can be readily taken from the package, and while stuck to skin, the opportunity for the adhesive patch to be rubbed against clothes and others is reduced, and therefore the edge thereof is hardly peeled and the adhesive patch can have a sufficient adhesive power to skin and hardly peels off from the skin surface.

Description Of Numeral References
1 Peripheral Part
2 Middle Part
3 Protrudent part
4 Connecting Built-up Part
5 Split Part
6 Support
7 Adhesive Layer
8 Release Liner

The invention claimed is:

1. An adhesive patch comprising a support, an adhesive layer containing a drug and arranged on at least one side of the support, and a release liner arranged on a side of the adhesive layer opposite to the side thereof on which the support is arranged,
   wherein the adhesive patch does not include bisoprolol,
   wherein the support, the release liner and the adhesive layer each have a rectangular planar shape and the adhesive patch as a whole has a rectangular planar shape,
   wherein, at one or more corners of the adhesive patch, the adhesive patch comprises a protrudent part on a support-side surface thereof,
   wherein each protrudent part is positioned at one of the corners of the adhesive patch,
   wherein the adhesive patch as a whole comprises a peripheral part and a middle part having a rectangular planar shape,
   wherein a thickness of the adhesive patch in the peripheral part is smaller than a thickness of the adhesive patch in the middle part, and the protrudent part is positioned at a corner of the middle part, and
   wherein each protrudent part is formed by thickening one or both of the support and the adhesive layer.

2. The adhesive patch as claimed in claim 1, wherein the adhesive patch comprises at least two protrudent parts and comprises, between said adjacent protrudent parts, a belt-like connecting built-up part in which a thickness of the adhesive patch is smaller than a thickness of the adhesive patch in the protrudent parts.

3. The adhesive patch as claimed in claim 1, wherein the protrudent part has a planar shape which is triangular, trapezoidal, crescent or semicircular.

4. The adhesive patch as claimed in claim 1, wherein the release liner comprises a split part that does not traverse the protrudent part.

5. The adhesive patch as claimed in claim 1, wherein the adhesive layer contains an organic liquid component.

6. The adhesive patch as claimed in claim 1, wherein the adhesive layer is not crosslinked.

7. The adhesive patch as claimed in claim 1, wherein the adhesive patch comprises at least two protrudent parts and comprises, between said adjacent protrudent parts, a belt-like connecting built-up part, wherein the thickness of the adhesive patch in the belt-like connecting built-up part is less than the thickness of the adhesive patch in the protrudent parts and greater than the thickness of the adhesive patch in the middle part.

* * * * *